United States Patent [19]

Giorgi et al.

[11] Patent Number: 4,886,791
[45] Date of Patent: Dec. 12, 1989

[54] SOLUBLE DERIVATIVES OF SILYBIN, A METHOD OF PREPARING THEM, AND PHARMACEUTICAL COMPOSITIONS CONTAINING THEM

[75] Inventors: Raffaello Giorgi; Marisa Conti; Giorgio Pifferi, all of Milan, Italy

[73] Assignee: Inverni della Beffa S.p.A., Milan, Italy

[21] Appl. No.: 219,058

[22] Filed: Jul. 13, 1988

[30] Foreign Application Priority Data

Jul. 17, 1987 [GB] United Kingdom ............... 8716918

[51] Int. Cl.[4] .................. A61K 31/335; C07D 319/20
[52] U.S. Cl. .................................... 514/100; 549/220
[58] Field of Search ............... 549/362, 220; 514/452, 514/100

[56] References Cited

PUBLICATIONS

The Merck Index, 10th edition, Merck & Co., Inc., Rahway, N.J., U.S.A., 1983, p. 1224, No. 8372.

*Primary Examiner*—Nicky Chan
*Attorney, Agent, or Firm*—Kirschstein, Ottinger, Israel & Schiffmiller

[57] ABSTRACT

Novel water-soluble derivatives of silybin of enhanced activity are provided as well as methods of preparing the derivatives and pharmaceutical compositions containing them. The novel derivatives according to the invention have the following general formula (I);

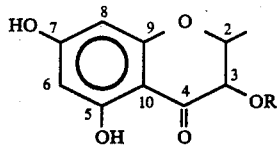

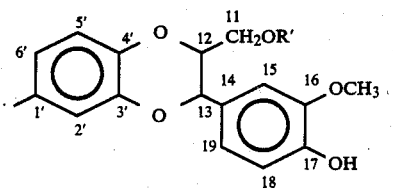

where: R=H or PO(OH)$_2$ and R'=PO(OH)$_2$

The compounds of the invention are useful inter alia in therapy of liver disorders and other applications where an anti-radical effect is required. They have the advantages of high hydrophilicity and are soluble at approximately pH 4, compared to prior art compounds which are water-soluble only at higher pH and enhanced stability.

5 Claims, No Drawings

SOLUBLE DERIVATIVES OF SILYBIN, A METHOD OF PREPARING THEM, AND PHARMACEUTICAL COMPOSITIONS CONTAINING THEM

This invention relates to novel derivatives of silybin, methods of preparing them, and pharmaceutical compositions containing them.

Silymarin, an extract from seeds of Silybum marianum, is used therapeutically as an antihepatotoxic agent and consists mainly of a mixture of three flavanolignanes—silybin, silydianin and silycristin. Among these, silybin is the active component which is present in the highest proportion.

The therapeutic use of silymarin is partly limited by its insolubility in water, so that it cannot be prepared in injectable form. In a first attempt to overcome this limitation, silybin was converted into hemiesters of dicarboxylic acids, as described in DE-1963318 (June 24, 1971)—Schwabe and DE-3442639 (May 22, 1986)—Madaus.

The present invention relates to new water-soluble derivatives of silybin of enhanced activity, to methods of preparing them, and to pharmaceutical compositions suitable for using them in initial treatment and maintenance therapy.

The novel derivatives according to the invention have the following general formula;

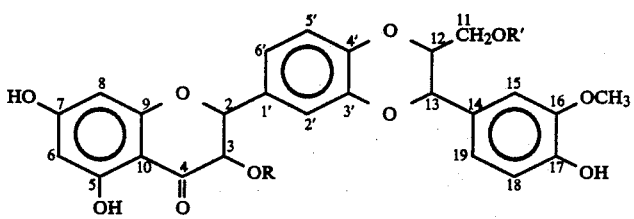

(I) where R=H {formula (Ia)} or PO(OH)$_2$ {formula (Ib)} and R'=PO(OH)$_2$.

The aforementioned compounds can be administered as such or in the form of pharmaceutically acceptable salts, i.e. salts with pharmaceutically acceptable cations. Non-limitative examples of such salts are salts of sodium, potassium, magnesium and ammonium and salts formed with basic amino acids.

The structures of the compounds of the invention can be assigned by NMR spectrum analysis thereof and of the corresponding diethyl esters (I, with R and/or R'=PO(OEt)$_2$), compared with the corresponding spectra for silybin.

One particularly surprising feature of the invention is that the silybin molecule can be solubilized if the primary and/or secondary alcoholic groups of the flavanolignane nucleus are selectively esterified with phosphoric acid.

One advantage is the greater hydrophilicity of the new molecule, which becomes soluble at approximately pH 4, whereas the corresponding known hemisuccinates become soluble at higher pH.

Another advantageous feature of the invention is that the synthesized phosphoric esters have greater chemical stability than the previously-mentioned organic esters, yet in vivo can be metabolized to silybin. The esters can therefore act either as such or as "prodrugs" which liberate silybin in vivo by using the phosphatases which are concentrated in a number of animal tissues, e.g. in the plasma, liver and brain.

Among the compounds claimed in the present patent specification, the preferred compound is the phosphoric monoester in position 11 (Ia), which may be obtained by selective esterification of the primary alcohol group of silybin, as well as pharmaceutically acceptable salts of this ester.

The compounds of the invention may be prepared by reacting silybin or an ester-forming derivative thereof with a phosphorylating agent, followed by (i) isolating a compound of formula (Ia) from the reaction mixture and/or (ii) continuing the phosphorylation until a 3,11-diester of formula (Ib) is formed and isolating said diester.

The 11-monoester may also be formed by continuing the phosphorylation until a 3,11-diester of formula (Ib) is formed and then subjecting the 3,11-diester to partial hydrolysis so as to form an 11-ester of formula (Ia).

The aforementioned reaction steps make use of the fact that the primary hydroxyl group in position 11 is more readily esterified than the secondary hydroxyl group in position 3. Consequently during the phosphorylation step, the 11-monoester is formed initially and the 3,11-diester forms on exhaustive phosphorylation. On partial saponification, the 3,11-diester is selectively converted to 11-monoester.

In one method of synthesizing compounds of formula (Ia) and (Ib), silybin may be dissolved in an excess of phosphorylating agent, preferably phosphorus oxychloride (alternatively silybin can be suspended in a suitable aprotic solvent and a phosphorylating reagent can be added, e.g. phosphorus pentachloride, dichloromethoxyphosphate, diphenylchlorophosphate or dibenzylchlorophosphate). The mixture is kept in an inert gas at a temperature of 10° to 60° C. for a time which varies with the chosen temperature—e.g. about 30 minutes at 50° or 20–30 hours at 20°. At the end of the reaction the solution is poured into a mixture of ice/water, from which the formed phosphoric ester(s) may be obtained by filtration in vacuo. The product(s) may be purified by dissolving in 5% sodium hydroxide solution and fractional reprecipitation at controlled pH.

Reaction at comparatively vigorous conditions (i.e. relatively high temperatures) or for relatively long periods of time favours production of 3,11-diester. Reaction at milder conditions favours production of 11-monoester.

Alternatively, 3,11-diester may be formed as described above and then subjected to partial hydrolysis.

If the reaction mixture from the phosphorylation steps is treated with an alcohol, e.g. cold ethyl alcohol, instead of pouring it into ice/water, the corresponding diethyl esters are obtained, i.e. compounds of formula (I) where R' is PO(OEt)$_2$ and R may be H or PO(OEt)$_2$.

These diethyl esters can be used as reference substances for determining the structure of the formed products.

The phosphoric acid esters (Ia and Ib) can be converted into the corresponding salts (e.g. salts in common pharmaceutical use) by solubilizing in water with the chosen base and subsequently recovering the desired salt by freeze-drying. Alternatively, esters (Ia and Ib) may be converted into salts with inorganic or organic bases, followed by precipitation with a suitable solvent, e.g. ethanol or acetone.

In order to test its pharmacological activity, compound (Ia) has been administered intravenously and orally in liver poisoning tests, such as the praseodymium poisoning test on the rat and the phalloidine poisoning test on the mouse, both tests being widely described in the literature for use in studying the antihepatotoxic effect of silymarin and silybin (Vogel, in "Studies in Organic Chemistry, Vol. 11, Flavonoids and Bioflavonoids, page 461, Elsevier 1982).

Compound (Ia), when intravenously administered, had much higher pharmacological activity than silybin dihemisuccinate, used as a reference substance. When orally administered, the antihepatotoxic activity was greater than that of silybin.

Owing to their marked solubility in water and powerful intravenous effect, the compounds of the invention are particularly suitable for emergency treatment of acute liver poisoning. Owing to their demonstrated oral activity, they can also be used in various kinds of chronic liver disorders. It is believed that the surprising efficiency of the compounds is based on a number of mechanisms, derivable at least in part from those attributed to silymarin and silybin, i.e. protection of the cellular membranes, stimulation of RNA polymerase A and protein synthesis, and inhibition of lipid peroxydase (Cavallini et al., Pharm. Res. Comm. 10, 133, 1978; Strubelt et al., Arzneim. Forsch. 30, 1690, 1980; Vogel, Studies in Organic Chemistry, Vol. 11: Flavonoids and Bioflavonoids p. 461, Elsevier, 1982, Sonnenbichler et al., ibidem p. 475).

The latter mechanism indicates that the phosphoric esters of silybin according to the invention may also be of use in prevention and treatment of diseases caused by free radicals, e.g. injury resulting from re-perfusion after ischaemic states in the heart or brain or liver area, or states of shock and syndromes associated with aging.

PHARMACOLOGICAL DATA

Table 1 shows the activity of silybin 11-phosphate (Ia) after liver poisoning by praseodymium by the method described by Vogel et al. (Arzneim. Forsch. 25, 82, 1975 and 25, 179, 1975). Silybin 11-phosphate was intravenously administered one hour before the praseodymium (10 mg/kg i.v.). At a dose equal to 1/26 of the LD50, determined intravenously in the same species (Table 4), (Ia) inhibited the increase in activity of the two serum transaminases and the increase in the weight of the liver and the hepatic triglycerides. Activity was maintained even at a dose of 1/65 of the LD50. A comparison between Ia and silybin dihemisuccinate was particularly favourable; the dose of silybin dihemisuccinate for preventing praseodymium poisoning was high—1/12 of the LD50 reported in the literature (Table 4) whereas there was no activity at lower doses comparable with those used for showing the activity of compound (Ia).

Table 2 shows the protective activity against poisoning with phalloidine. In this extremely severe test (Tuchweber et al., Toxicol. Appl. Parmacol., 51, 265, 1979), compound (Ia) was injected one hour before phalloidine (3 mg/kg i.p.) and protected all the mice from death, at a dose equal to 1/15 of the LD50 i.v. in the mouse (Table 4). Silybin dihemisuccinate, when tested at a dose equal to 1/13 of the LD50 i.v. in the mouse, protected only 60% of the mice from death by phalloidine (Table 4). Even at higher doses than those given in the Table (63 and 126 mg/kg i.v.), silybin 11-phosphate was markedly superior to silybin dihemisuccinate.

Table 3 shows the activity after oral administration simultaneously with injection of praseodymium. Compound (Ia) was as active as silybin dihemisuccinate in counteracting the increase in the two serum transaminases induced by praseodymium, but was considerably more active than silybin alone.

TABLE 1

Antihepatotoxic activity of silybin 11-phosphate in the praseodymium test on the rat (i.v. administration)

| Treatment | Dose mg/kg | No. of Animals | SERUM ENZYMES ASAT U/L m ± s.e. | ALAT U/L m ± s.e. | LIVER Wt (g) m ± s.e. | Triglycerides m ± s.e. |
|---|---|---|---|---|---|---|
| Controls | — | 10 | 80.9 ± 5.8** | 23.8 + 3.3** | 8.4 ± 0.2** | 1237.3 ± 231.2** |
| Praseodymium | — | 10 | 1886.7 ± 493.5 | 1726.7 ± 466.9 | 14.0 ± 0.2 | 8117.7 ± 231.2 |
| Silybin 11-phosphate (Ia) | 6.32(1) | 10 | 877.0 ± 420.5 (−54) | 495.0 ± 244.6* (−71) | 12.6 ± 0.5 (−10) | 4792.4 ± 1068.8* (−41) |
| Silybin dihemisuccinate | 7.5(1) | 10 | 1672.0 ± 292.8 (−11) | 1366. ± 343.1 (−21) | 12.6 ± 0.5 (−3) | 6692.8 ± 738.3 (−18) |
| Controls | — | 12 | 84.8 ± 3.6** | 25.3 ± 1.8** | 7.9 ± 0.1** | 1487.2 ± 499.4** |
| Praseodymium | — | 12 | 1887.0 ± 347.1 | 1208.3 ± 244.6 | 12.5 ± 0.2 | 8751.0 ± 806.1 |
| Silybin phosphate (Ia) | 15.8(2) | 12 | 90.9 ± 8.9** (−95) | 31.3 ± 3.2** (−97) | 8.7 ± 0.2** (−30) | 672.7 ± 100.5** (−92) |
| Silybin dihemisuccinate | 37.5(3) | 12 | 2600.0 ± 570.9 (+38) | 1988.3 ± 465.3 (+64) | 12.6 ± 0.4 (+1) | 7083.9 ± 747.5 (−19) |
| Silybin dihemisuccinate | 75(4) | 12 | 887.0 ± 63.1** (−53) | 422.9 ± 85.6** (−65) | 12.1 ± 0.5 (−1) | 9221.0 ± 910.4 (+11) |

**$p < 0.01$ Dunnett's "T" test using praseodymium
Percentage variations relative to the praseodymium group are shown in brackets
(1)Corresponds to 5 mg of silybin
(2)Corresponds to 2.5 mg of silybin

TABLE 2

Antihepatotoxic activity of silybin 11-phosphate on the mouse poisoned with phalloidine (i.v. administration)

| Treatment (10 animals/group) | Dose mg/kg | Death Rate | Percentage of deaths |
|---|---|---|---|
| Controls | — | 0 | 0 |
| Phalloidine | — | 7 | 70 |
| Silybin 11-phosphate (Ia) | 15.8(1) | 0 | 0 |
| Silybin dihemisuccinate | 75.0(2) | 4 | 40 |

(1) Corresponds to 12.5 mg silybin
(2) Corresponds to 50.0 mg silybin

TABLE 3

Antihepatotoxic activity of silybin 11-phosphate in the praseodymium test on the rat (oral administration)

| | | Serum Enzymes | |
|---|---|---|---|
| Treatment (12 animals/group) | Dose mg/kg | ASAT U/L m ± s.e. | ALAT U/L m ± s.e. |
| Controls | — | 115.2 ± 6.0* | 32.1 ± 2.8* |
| Praseodymium | — | 3758.3 ± 840.0 | 3566.7 ± 832.3 |
| Silybin 11-phosphate (Ia) | 315(1) | 931.7 ± 299.0** (−75) | 783.3 ± 304.6** (−78) |
| Silybin dihemisuccinate | 375(1) | 1118.3 ± 512.0** (−70) | 886.7 ± 395.1** (−75) |
| Silybin | 250 | 3680.2 ± 885.6 (−2) | 3620 ± 795.8 (+1) |

**p < 0.01 Dunnett's "t" test using praseodymium
Percentage variations relative to the praseodymium group are shown in brackets.
(1) Corresponds to 250 mg of silybin

татBLE 4

Acute toxicity of silybin 11-phosphate and silybin dihemisuccinate

| Substance | Animals | Method of Administration | LD50 (mg/kg) |
|---|---|---|---|
| Silybin 11-phosphate (Ia, sodium salt) | Mouse | i.v. | 235(174–291) |
| | | os | 3000 |
| | Rat | i.v. | 415(378–457) |
| | | os | 3000 |
| Silybin dihemisuccinate | Mouse | i.v. | 970(1) (931–1010) |
| | | os | 3000 |
| | Rat | i.v. | 920(1) (906–940) |

(1) A. Desplaces et al., Arzneim. Forsch., 25, 89, 1975.

1. Hypobaric anoxia

Table 5 gives data showing the effect of compound Ia on the survival time of mice subjected to hypobaric anoxia. In this test (M. Nakanishi et al., Life Sciences, 13, 467, 1973), compound Ia was intraperitoneally injected half an hour before the anoxia.

As the data show, compound Ia is active in prolonging the survival time and significantly more active than succinylsilybin used as a reference standard.

TABLE 5

Protective effect of silybin-11-phosphate on survival time of mice subjected to hypoxia (i.p. administration).

| Treatment | No. of Animals | Survival Time ED50 mg/kg i.p. (Confidence limits p = 0.95) |
|---|---|---|
| Silybin 11-phosphate | 48 | 45.7 (27.7–75.2) corresponds to 36.3 mg/kg silybin |
| Silybin dihemisuccinate | 36 | 107.7 (137.1–212.6) corresponds to 97.3 mg/kg silybin |

2. Anti-radical activity

The anti-radical activity of compound Ia was measured "in vitro" by testing the disappearance of the free 1,1-diphenyl-2-picrylhydrazyl (DPPH) radical (J. Pincemail et al., Stud. Org. Chem. 23, 423, 1985). The results in Table 6 show that compound Ia is significantly active in destroying free radicals and is about 3.5 times more active than either silybin or succinylsilybin.

TABLE 6

Free radical scavenging effect of silybin-11-phosphate (DPPH method).

| Substance | $IC_{50}$ μM (confidence limits p = 0.95) |
|---|---|
| Silybin 11-phosphate (Ia) | 106.8 (104.2–109.0) corresponds to 85 μM silybin |
| Silybin | 327.0 (287.5–373.0) |
| Silybin dihemisuccinate | 564.8 (518.7–614.9) corresponds to 322 μM silybin |

The compounds according to the invention can be suitably formulated for oral or rectal administration or in injectable form, using conventional technologies and excipients such as those give in Remington's Pharmaceutical Sciences, Mack Pub. Co. New York, U.S.A.

The following formulations are non-limitative examples:

100 mg tablet containing 12.6 mg silybin 11-phosphate, sodium salt

| | |
|---|---|
| Silybin 11-phosphate, sodium salt | 12.6 mg |
| Lactose | 50.4 mg |
| Microcrystalline cellulose | 30.0 mg |
| Sodium carboxymethyl cellulose | 5.0 mg |
| Talcum | 1.0 |
| Magnesium stearate | 1.0 |

Ampoule containing 12.6 mg silybin 11-phosphate, sodium salt

| Freeze-dried ampoule | |
|---|---|
| Silybin 11-phosphate, sodium salt | 12.6 mg |
| Mannitol | 40.0 mg |
| Ampoule of solvent | |
| Sodium chloride | 9.4 mg |
| Water for injectable preparation, qs ad | 2.0 ml |

It will thus be appreciated that the invention further provides a method for the prevention and treatment of injuries, diseases or pathological conditions caused by free radicals which comprises administering an effective amount of a compound of formula I.

The method is particularly applicable in the treatment of injuries resulting from re-perfusion after ischaemic states in the heart, brain or liver; states of shock and syndromes associated with aging.

The invention further provides a method for the treatment of acute and chronic liver diseases of toxic, metabolic and/or infective origin or of degenerative nature, and for prevention of liver damage resulting from the use of drugs and/or luxury substances (e.g. alcohol and fatty food) injurious to the liver, which comprises administering an effective amount of a compound of formula I.

For treating humans, a suitable daily does is from 0.4 mg/kg to 40 mg/kg, preferably 1 mg/kg to 10 mg/kg.

The following examples non-limitatively illustrate the invention:

EXAMPLE 1

Silybin 11-phosphate (Ia)

In a stream of nitrogen, 150 g (0.31 mols) of silybin were suspended in 750 ml (0.82 mols) of phosphorus oxychloride and agitated at 20°–22° C. for 30 hours. The suspension gradually changed into a dark solution and the disappearance of the starting silybin was checked by TLC. After 30 hours, the reaction mixture was poured directly into ice/water and the aqueous suspension was agitated to bring about complete destruction of the phosphorylating agent, keeping the temperature at 20° C. The product was filtered in vacuo and washed on the filter with water until the chlorides disappeared.

The solid was purified firstly by suspension in water under nitrogen and secondly by bringing the suspension to pH 7 by adding a 5% sodium hydroxide solution. The resulting solution was filtered on Celite and then acidified to pH 1.2 with 18% hydrochloric acid. The precipitate was collected, washed on the filter with water, and dried at 50° C. in vacuo.

150 grams (an 85% yield) of (Ia) were obtained as a light cream-coloured crystalline solid having the following analytical characteristics:

m.p. 200°–210° C.

$[\alpha]_D^{20} + 28°$ (conc 0.5%, $CH_3OH$)

$E_{1cm}$ (350 nm) 287 (MeOH)

| Elementary analysis: for $C_{25}H_{23}O_{13}P$ | | | |
| --- | --- | --- | --- |
|  | C | H | P |
| % calculated | 53.34 | 4.12 | 5.51 |
| % found | 53.00 | 4.24 | 5.32 |

MS (FAB, negative ions): m/z 561 ($M^-$. $-H\cdot$).

$^{13}C$—NMR: (DMSO-$d_6$) 197.5 (C-4), 166.8 (C-7), 163.2 (C-5), 162.4 (C-9), 147.6 (C-16), 147.1 (C-17), 143.0 (C-4′), 130.3 (C-1′), 126.7 (C-14), 121.4 (C-19), 120.5 (C-6′), 116.4 (C-5′), 116.4 (C-18), 115.5 (C-2′), 111.7 (C-15), 100.4 (C-10), 96.2 (C-6), 95.1 (C-8), 82.5 (C-2), 75.5 (C-12), 75.4 (C-13), 71.4 (C-3), 63.0 (C-11), 55.6 (OMe).

EXAMPLE 2

Preparation of sodium salt of silybin 11-phosphate (Ia, sodium salt)

In a nitrogen atmosphere, 150 g (0.27 mols) of (Ia) were dissolved in 1.5 liters of deionized water and 0.75 liters of acetone, the resulting solution being cooled to 0°–4° C. About 300 ml of a 5% NaOH solution were added dropwise, bringing the pH of the solution to 6.5. The acetone was evaporated in vacuo at 30° C. The aqueous solution was filtered on a Celite panel and freeze-dried.

146 g of product (a 92% yield) were obtained as a light-coloured solid having the following analytical charcteristics:

m.p. 220°–225° C.

$[\alpha]_D^{20} + 20°$ (conc 0,25%, $CH_3OH$)

$E_1\%_{cm}$ (370 nm) 287 (MeOH).

EXAMPLE 3

Preparation of the diethyl ester of silybin 11-phosphate (Ia, R=H, R′=PO(OC$_2$H$_5$)$_2$)

A suspension of 15 g (0.031 mols) of silybin in 75 ml (0.82 mols) of phosphorus oxychloride was kept agitated in a nitrogen atmosphere at 20°–22° C. for 30 hours. The resulting dark solution was poured into an excess of absolute ethanol cooled to $-10°$ C. The solution was agitated for an hour and then poured into water and extracted with ethyl acetate. The organic phase was washed with water, dried on sodium sulphate and evaporated in vacuo. The residue was crystallised from ethyl acetate and petroleum ether and the solid was dried in vacuo at 40° C. until its weight was constant. 15 g of product (a 78% yield) were obtained as an amorphous light cream-coloured solid having the following properties:

m.p. 160°–162°.

$E_{1cm}^{1\%}$ (330 nm) 287 (MeOH).

| Elementary analysis: for $C_{29}H_{31}O_{13}P$ | |
| --- | --- |
|  | P |
| % calculated | 5.02 |
| % found | 4.98 |

Molecular peak in the mass spectrum (FAB) at m/z 618.

Spectrum $^{13}C$—NMR (DMSO-$d_6$): 197.4 (C-4), 166.8 (C-7), 163.3 (C-5), 162.4 (C-9), 147.7 (C-16), 147.4 (C-17), 143.0 (C-4′), 143.0 (C-3′), 130.5 (C-1′), 126.6 (C-14), 121.4 (C-19), 120.6 (C-6′), 116.6 (C-5′), 116.3 (C-18), 115.4 (C-2′), 111.8 (C-15), 100.4 (C-10), 96.1 (C-6), 95.0 (C-8), 82.4 (C-2), 75.8 (C-12), 75.4 (C-13), 71.5 (C-3), 63.0 (POCH$_2$CH$_3$), 62.0 (C-11), 55.7 (OMe), 15.9 (POCH$_2$CH$_3$).

We claim:

1. A compound of the general formula I

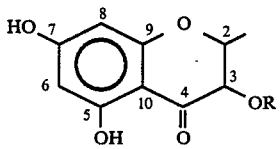

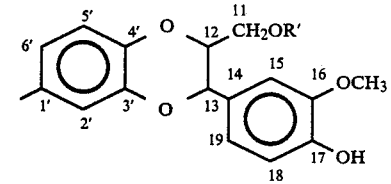

wherein R=H or PO(OH)$_2$ and R′=PO(OH)$_2$ or a pharmaceutically acceptable salt thereof.

2. A compound according to claim 1 wherein R=H, or a pharmaceutically acceptable salt thereof.

3. A compound according to claim 1 wherein said salt is a sodium, potassium, magnesium or ammonium salt or a salt with a basic amino acid.

4. A pharmaceutical composition comprising a compound according to claim 1 and a pharmaceutically acceptable excipient.

5. A pharmaceutical composition according to claim 4 in a form adapted for oral, rectal or parenteral administration.

* * * * *